United States Patent [19]

Gruber et al.

[11] 4,203,919
[45] May 20, 1980

[54] (ACETOXYALKYL) 2-CYANO-3,3-DIPHENYLACRYLATE INTERMEDIATES FOR MAKING COPOLYMERIZABLE, ULTRAVIOLET LIGHT ABSORBER COMPOUNDS

[75] Inventors: Bruce A. Gruber, Bloomingdale; Donald H. Lorenz, Basking Ridge, both of N.J.

[73] Assignee: GAF Corporation, New York, N.Y.

[21] Appl. No.: 35,648

[22] Filed: May 3, 1979

[51] Int. Cl.$^2$ .......................................... C07C 121/70
[52] U.S. Cl. ...................... 260/465 D; 260/45.85 A; 260/465.4
[58] Field of Search .................................. 260/465 D

[56] References Cited

U.S. PATENT DOCUMENTS 3,644,466   2/1972   Strobel et al. .................. 260/465 D

*Primary Examiner*—Dolph H. Torrence
*Attorney, Agent, or Firm*—Walter C. Kehm; Walter Katz

[57] ABSTRACT

This invention relates to (acetoxyalkyl) 2-cyano-3,3-diphenylacrylate intermediates having the formula:

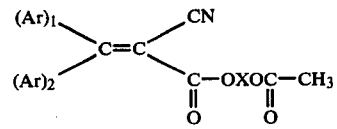

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl; and, X is alkylene, $C_2$–$C_{17}$, unsubstituted or substituted with halo, cyano, alkyl, $C_1$–$C_6$, alkoxy, $C_1$–$C_6$, alkoxyalkyl, $C_1$–$C_6$ or alkoxyalkyleneoxy, $C_1$–$C_6$.

These intermediates are used in making (2-cyano-3,3-diphenylacryloxy) alkylene acrylic esters and (2-cyano-3,3-diphenyl) alkylene ethylenic ethers, which compounds are copolymerizable, ultraviolet light absorbers.

The intermediate compounds are made by:
(a) acylating a hydroxyalkylene cyanoacetate with an acylating agent to form an acylated intermediate whose hydroxy radical is protected by an acyl group which is convertible to hydroxy by hydrolysis, and
(b) condensing the acyl intermediate with a benzophenone.

6 Claims, No Drawings

(ACETOXYALKYL) 2-CYANO-3,3-DIPHENYLACRYLATE INTERMEDIATES FOR MAKING COPOLYMERIZABLE, ULTRAVIOLET LIGHT ABSORBER COMPOUNDS

BACKGROUND OF THE INVENTION

1. Field of the Invention

This invention relates to ultraviolet light absorber compounds and, more particularly, to (acetoxylakyl) 2-cyano-3,3-diphenylacrylate intermediates. The intermediates herein are used to make compounds which copolymerize with vinyl monomers to produce polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiation as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,714. These ultraviolet absorbers are mechanically mixed with the plastic materials to prevent discoloration and degradation of the material. However it has been observed that such absorbers sometimes fail or are blocked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

RELATED PATENT APPLICATIONS (a) Ser. No. 006,787, filed Jan. 26, 1979 by the same applicants, and assigned to the same assignee as herein. This application described novel copolymerizable ultraviolet light absorber compounds, which are substantially free of the disadvantages of the prior art, which are (2-cyano-3,3-diphenyl acryloxy) alkylene acrylic acid esters.

(b) Ser. No. 016,134, filed Mar. 1, 1979, by the same applicants, and assigned to the same assignee, as herein. This application describes a method of making the compounds referred to in related application Ser. No. 006,787 above.

(c) Ser. No. 022,320, filed Mar. 19, 1979, by the same applicants, and assigned to the same assignee, as herein. This application describes novel copolymerizable ultraviolet light absorber compounds, which are (2-cyano-3,3-diphenylacryloxy)alkylene ethylenic ethers.

This application is a continuation in part of the above related patent applications.

SUMMARY OF THE INVENTION

What is provided herein are intermediates in the synthesis of copolymerizable ultraviolet light absorber compounds which are (2-cyano-3,3-diphenylacryloxy) alkylene acrylic acid esters or (2-cyano-3,3-diphenyl) alkylene ethylenic ethers. The intermediates have the formula:

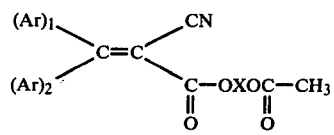

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl; and, X is alkylene, $C_2$-$C_{17}$, unsubstituted or substituted with halo, cyano, alkyl, $C_1$-$C_6$ alkoxyalkyl, $C_1C_6$, alkoxyalkyleneoxy, $C_1$-$C_6$.

The method of making the intermediate comprises:

(a) acylating hydroxyalkylene cyanoacetate with an acylating agent to form an acylated intermediate whose hydroxy radical is protected by an acyl group which is convertible to hydroxy by hydrolysis, and, (b) condensing the acyl intermediate with a benzophenone.

DETAILED DESCRIPTION OF THE INVENTION

Suitable $(Ar)_1$ and $(Ar)_2$ groups are given in U.S. Pat. No. 3,644,466, including representative starting benzophenone compounds. In the best mode of the invention both $(Ar)_1$ and $(Ar)_2$ are phenyl.

The X groups are unsubstituted or substituted alkylene radicals, $C_2$-$C_{17}$. The preferred groups are unsubstituted lower alkylene, $C_2$-$C_6$, which are derived synthetically from ethylene glycol, propylene glycol, butanediol, and the like. The best mode is represented by —$CH_2$—$CH_2$.

In the method of preparing the intermediates of the group of the hydroxyalkyl cyanoacetate starting material first is protected by acylation to form an acyl group which is convertible by hydrolysis to the hydroxy compound. Acylation is carried out with cetate anhydride or acetyl chloride, usually, to provide the corresponding acetoxyalkyl cyanoacetate. The protected compound then is condensed with a benzophenone in a Knoevenagel reaction to provide the acetoxyalkyl (2-cyano-3,3-diphenyl) acrylate in excellent yield.

Hydrolysis of the protecting acetyl group affords the corresponding hydroxyalkyl (2-cyano-3,3-diphenyl) acrylate intermediate, which is then directly esterified, for example, with a suitable acryloyl halide or acrylic acid to give the desired (2-cyano-3,3-diphenylacryloyloxy) alkylene acrylic acid ester compounds.

This method of the invention is summarized in the flow sheet below where X and Y are as defined above, and Z is a halide or hydroxyl group.

Typical X groups are —$CH_2CH_2$, —$CH_2CH_2CH_2$—, —$CH_2CH_2CH_2CH_2$—, and the like.

METHOD OF INVENTION

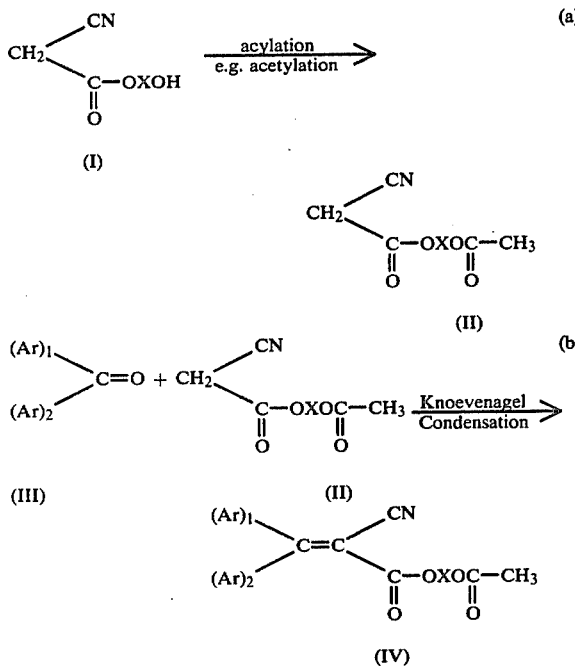

The hydroxyalkyl cyanoacetate starting material (I) for step (a) is prepared by reacting cyanoacetic acid with a lower dihydric alcohol as described in U.S. Pat. No. 3,644,466, Example 3, cols. 7-8.

In step (a), the hydroxy group of the hydroxyalkyl cyanoacetate (I) is protected by acylation, suitably by acetylation with acetic anhydride, to give the corresponding acetoxyalkyl cyanoacetate intermediate (II).

Step (b) in the process comprises a Knoevenagel condensation of a suitable benzophenone (III) with (II) to produce an acetoxyalkyl (2-cyano-3,3-diphenyl) acrylate (IV). The Knoevenagel reaction is generally run in the presence of a solvent, such as benzene, toluene, or thylenedichloride, under reflux, usually at a temperature between 80° and 100° C. for about 24 hours. The reaction preferably proceeds in a nitrogen atmosphere and in the presence of glacial acetic acid and ammonium acetate as a catalyst. Conventional washings of the product with water and saturated bicarbonate solution are done prior to the drying, removing the solvent, and recovering the product.

The final compounds prepared from the intermediates of the invention are copolymerized, for example, with a urethane oligomer, by radiation curing, to provide useful polymeric coatings.

The following examples will describe the invention with more particularity.

EXAMPLE 1

(2-Acetoxyethyl) 2-Cyano-3,3-Diphenylacrylate (a) 2-Acetoxyethyl 2-Cyanoacetate

Cyanoacetic acid was esterified with ethylene glycol according to U.S. Pat. No. 3,644,466 (Col. 7-8, Ex. 3) to give the 2-hydroxyethyl 2-cyanoacetate starting material in 74% yield.

Into a 1 l. three-neck round bottom flask with magnetic stirrer, dropping funnel, thermometer, and drying tube was charged 122 g. (1.2 moles) of acetic anhydride and 10 drops of concentrated sulfuric acid. Then 129 g. (1 mile) of 2-hydroxyethyl cyanoacetate was added dropwise with stirring while maintaining the reaction temperature below 75° C. The acylated ester thus produced was then diluted with 100 ml. of water and the excess acid was neutralized with solid potassium carbonate. The oil layer was separated and dried to yield 130 g. (79%) of the desired compound.

(b) A 1 l. three-neck round bottom flask fitted with a mechanical stirrer, a thermometer and a Dean-Stark trap fitted with a reflux condenser was charged with 200 ml. of toluene, 182 g. (1 mole) of benzophenone, 205 g. (1.2 moles) of 2-acetoxyethyl 2-cyanoacetate, 40 ml. of glacial acetic acid, 16 g. of ammonium acetate. The contents were heated to reflux (110° C.) for 24 hours while the theoretical amount of water by-product was removed by azeotropic distillation. Upon removal of the solvent, as well as unreacted starting material by vacuum distillation, a yield of 200 g. (60%) of the desired product was obtained.

EXAMPLE 2

(3-Acetoxypropyl) 2-Cyano-3,3-Diphenyl Acrylate

Using an equivalent amount of propylene glycol in place of ethylene glycol in Step (a) of Example 1, the desired 3-acetoxypropyl compound is obtained in comparable yeild.

EXAMPLE 3

4-(Acetoxybutyl) 2-Cyano-3,3-Diphenylacrylate

Using an equivalent amount of 1,4-butanediol in place of ethylene glycol in Example 1, there is produced the desired 4-acetoxybutyl compound in comparable yield.

What is claimed is:

1. (Acetoxyalkyl) 2-cyano-3,3-diphenylacrylate intermediate compounds having the formula:

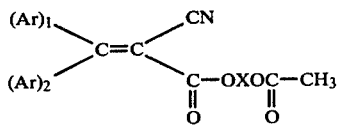

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl; and, X is alkylene, $C_2$-$C_{17}$, unsubstituted or substituted with halo, cyano, alkyl, $C_1$-$C_6$, alkoxy, $C_1$-$C_6$ alkoxyalkyl, $C_1$-$C_6$, or alkoxyalkyleneoxy, $C_1$-$C_6$.

2. An intermediate compound according to claim 1 in which both $(Ar)_1$ and $(Ar)_2$ are phenyl.

3. An intermediate compound according to claim 1 in which X is unsubstituted $C_1$-$C_6$.

4. An intermediate compound according to claim 1 which is (2-acetoxyethyl) 2-cyano-3,3-diphenylacrylate.

5. An intermediate compound according to claim 1 which is (3-acetoxypropyl) 2-cyano-3,3-diphenylacrylate.

6. A compound according to claim 1 which is (4-acetoxybutyl) 2-cyano-3,3-diphenylacrylate.

* * * * *